United States Patent [19]

Thorsson

[11] Patent Number: 4,886,751
[45] Date of Patent: Dec. 12, 1989

[54] PROCESS FOR THE PRODUCTION OF ETHANOL THROUGH MOLASSES FERMENTATION

[75] Inventor: Conny Thorsson, Älvsjö, Sweden

[73] Assignee: Nobel Chematur AB, Karlskoga, Sweden

[21] Appl. No.: 209,476

[22] PCT Filed: Oct. 30, 1986

[86] PCT No.: PCT/SE86/00498
§ 371 Date: Jun. 20, 1988
§ 102(e) Date: Jun. 20, 1988

[87] PCT Pub. No.: WO87/04724
PCT Pub. Date: Aug. 13, 1987

[30] Foreign Application Priority Data

Jan. 31, 1986 [SE] Sweden .............................. 8600429

[51] Int. Cl.$^4$ .............................................. C12P 7/06
[52] U.S. Cl. ..................................... 435/162; 435/161; 435/911
[58] Field of Search ........................ 435/161, 162, 911

[56] References Cited

U.S. PATENT DOCUMENTS

| | | | |
|---|---|---|---|
| 4,358,536 | 11/1982 | Thorsson et al. | 435/161 |
| 4,511,437 | 4/1985 | Heck et al. | 435/161 |
| 4,522,920 | 6/1985 | Thorsson et al. | 435/161 |
| 4,769,112 | 9/1988 | Wheldon | 435/161 |

OTHER PUBLICATIONS

Derwent Abs. 85-171994/29 DD-220045 (3-85) Khackmos et al.
Derwent Abs 88-119380/17 WO8802649 (4-88) Erickson.
Derwent Abs 86-157244/25 EP-185010 (6-86) Krenn.
Derwent Abs 83-49100k/20 WO8301627 (5-83) Wallner.

Primary Examiner—Herbert J. Lilling
Attorney, Agent, or Firm—Davis Hoxie Faithfull & Hapgood

[57] ABSTRACT

Ethanol is produced by fermentation of beet or cane sugar molasses in a fermentor. The ethanol formed in the fermentor is recovered by operating a primary distillation step (PD) in circulation circuit with the fermentor (FI). From the fermentor (FI) a mash stream (5) is continuously withdrawn, and after separation and recirculation of the yeast contained in the mash (5), the yeast-free mash is supplied to the primary distillation step (PD). A part (14) of the bottom stream (13) from the primary distillation step (PD) is recirculated to the fermentor. By controlling the water input to the process circuit so that the concentration of non-fermentable substance in the fermentor (FI) during a first period of time is increased from a start value in the range 5–15% by weight DS to a value in the range 20–30% by weight DS and maintaining the last high concentration during a second period of time so that the average content of non-fermentable substance in the fermentor during said two periods of time exceeds 20% by weight DS, a on average very concentrated stillage can continuously be discharged from the process.

8 Claims, 1 Drawing Sheet

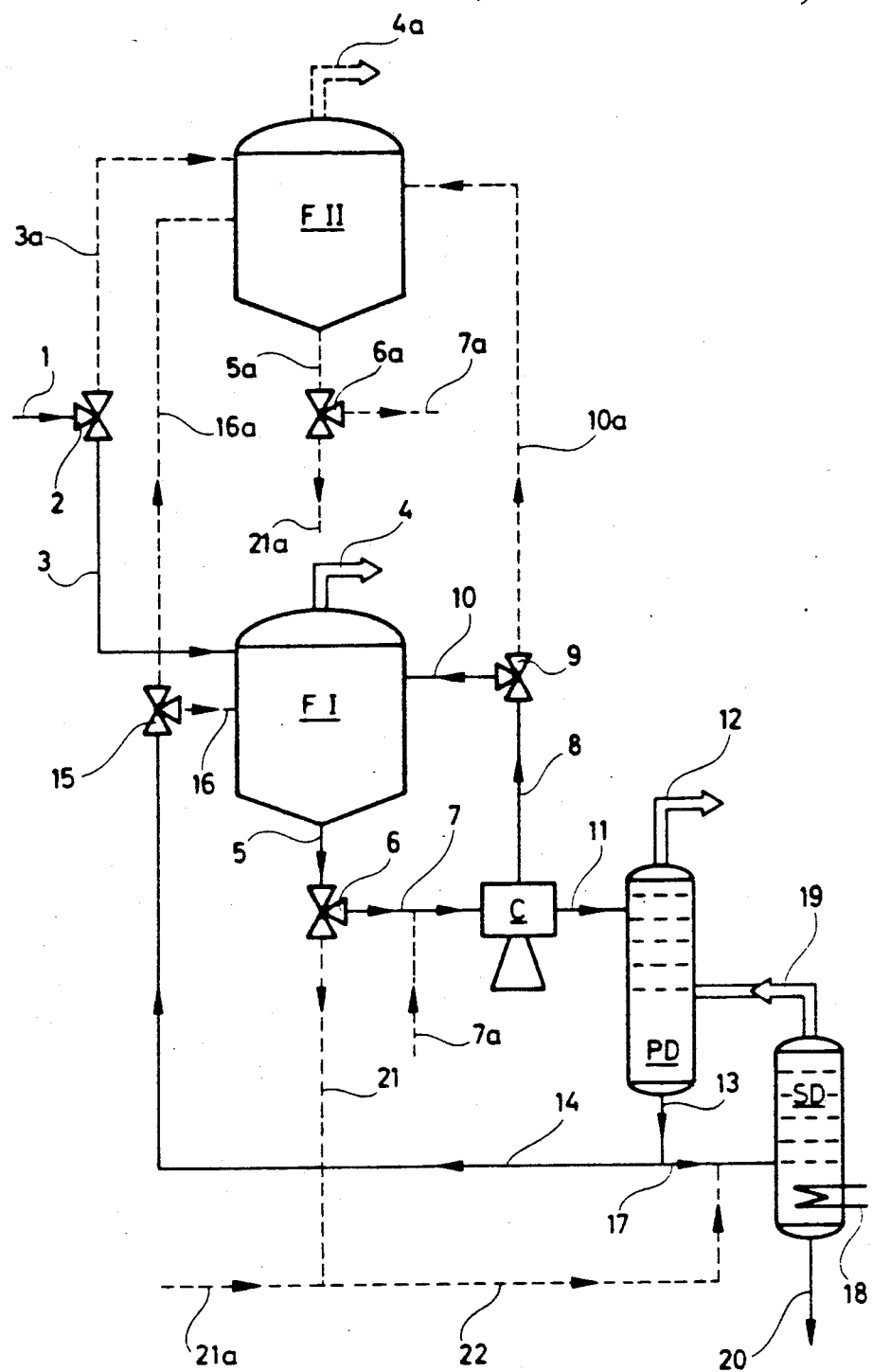

PROCESS FOR THE PRODUCTION OF ETHANOL THROUGH MOLASSES FERMENTATION

The present invention relates to a process for the production of ethanol through fermentation of a carbohydrate containing substrate in a fermentor during continuous discharge of a stream of fermentation liquor from the fermentor, which stream is separated in a centrifugal separation step into a yeast enriched stream, which is recirculated to the fermentor, and an essentially yeast-free stream, which in a primary distillation step is separated into an ethanol enriched top stream and a residual liquid bottom stream, of which a part is recirculated to the fermentor and the residual part is supplied to a secondary distillation step for stripping off remaining ethanol to form a concentrated stillage impoverished in ethanol.

In known processes of the above mentioned kind with continuous stillage recirculation and yeast recirculation, as disclosed for example in applicant's American Pat. No. 4,358,536, one essential advantage of the process is the low water input and the low energy costs associated therewith for evaporation of the stillage obtained as by-product. At a typical fermentation process with for example cane sugar molasses as raw material a stillage with a maximum dry substance content (DS) of non-fermentable material of about 10% by weight can be achieved, while in said continuous recirculation process normally a DS-content in the range of 22-25% by weight is reached in the stillage from the secondary distillation step, the DS-content in the fermentor being in the order of 15% by weight.

Mathematically, a further increase of the DS-content of the final stillage and thereby a further reduction of the evaporation energy required could be achieved by simply further reducing the water input to the process and increasing the fraction of the intermediate stillage recirculated from the primary distillation step. For the above mentioned continuous recirculation process the minimal required water input is settled by two essentially different criteria. One criterium emanates from the fact that a certain part of the non-fermentable substance contained in the raw material, the concentration of which increases with reduced water input to the fermentor, consists of osmosis forming dissolved salts and molecularly dissolved substances. Increasing concentration of osmosis forming substances in the fermentation liquor leads to a condition, at which the yeast growth rate is less than the rate with which the living yeast cells are killed off. The total ethanol productivity decreases due to reduced number of active yeast cells and also due to decreasing ethanol productivity of still active yeast cells.

The second criterium, which can be dimensioning for the water input, is set by the flow condition of the system. For example in case of fermentation on a grain raw material, which contains moderate amounts of soluble osmosis forming substances, the minimum water input limit is generally not set by the content of soluble substances but by the maximum content of insoluble substances for achieving the required fluidity in the system. In fermentation of certain sugar raw material, such as beet and cane sugar molasses, however, the fluidity conditions allow such a low water input that the fermentation almost completely stops due to a too high concentration of osmosis forming substances in the fermentor.

The object of the present invention is to modify the process for ethanol fermentation of the introductively mentioned kind so that a further, in dry substance concentrated stillage is obtained from the secondary distillation step.

This object has been reached in the process for ethanol fermentation on beet or cane sugar molasses and is primarily characterized in that the process water input is controlled, for example by controlling the concentration of the supplied molasses substrate, so that during a first period of time, the concentration of non-fermentable substance in the fermentor, calculated as water-free substance (DS) increases from a start value in the range 5-15% by weight DS to a value in the range 20-30% by weight DS, in which the range the ethanol productivity of the yeast is decreasing, whereafter the continuous fermentation and distillation with recirculation of said bottom stream is continued at last said high concentration of non-fermentable substance in the fermentor during a second period of time, so that the average concentration of non-fermentable substance in the fermentor during said two periods of time exceeds 20% by weight DS.

The term beet and cane sugar molasses refers in this application to different sugar containing by-fractions obtained in recovering sugar from sugar canes and sugar beets.

According to the present invention it has surprisingly been found that if the water input in ethanol fermentation on molasses is reduced compared with the water input used in the above mentioned known recirculation process and the concentration of the osmosis forming substances in the fermentor thereby is increased above the limit where yeast growth and maintenance of yeast ethanol productivity is no longer possible, nevertheless a certain, however decreasing, ethanol productivity can be maintained during such a long period of time, that a considerable increase in the average DS-content of the stillage can be achieved. In addition it has been found that the increase of the DS-content of the stillage and the evaporation costs saved therewith more than compensate the cost raising factors associated with the process modification from continuous fermentor operation during a long period of time at steady-state to a time limited operation period: More frequent starting up and emptying of the fermentor, cost for propagating a new yeast for each starting up, and fermentation in a fermentor environment giving a lower average ethanol productivity. In a long time fermentation of molasses at steady-state concentration in the range 10-18% by weight DS in the fermentor, an ethanol productivity of 8-15 kg ethanol per hour and $m^3$ fermentor liquid is generally achieved, while a lower average ethanol productivity of 5-9 $kg/m^3/h$ is obtained at the present process.

With decreasing ethanol productivity of the yeast is intended in this context the matter of state, at which a yeast population required for constant ethanol productivity cannot be maintained despite oxygen supply and nutrition supply to the fermentor liquor for promoting yeast growth.

By the modified process according to the invention several advantages of the original whole continuous recirculation process are maintained or reinforced. Thus, in comparison with other ethanol fermentation processes the present process is also characterized by the outstanding short residence time of 4-10 hours for the fermentation liquor in the fermentor, i.e. the average time before the liquor reaches the primary distillation step and is heated to about 80°–100° C. before a major part of it is returned in pasteurized condition to the fermentor. This contributes to a very low infection risk in the system. Besides, the infection risk is further reduced in the present process by the fact that the concentration of non-fermentable material and thereby the concentration of osmosis forming dissolved substances in the fermentor becomes higher than at any other known process giving a still more unfavourable environment for bacteria growth in the fermentor.

In the distillation plant, which in addition to the primary distillation step in circuit with the fermentor and the secondary distillation step connected to the first distillation step for final stripping of stillage, generally also includes successive distillation equipment for refining the ethanol containing vapour to desired concentration and quality, whole continuous operation with constant supply of ethanol to the primary distillation step is most often preferred. Therefore, according to a preferred embodiment of the invention, the fermentation is carried out in two alternating fermentors, which are started up and emptied with such a time-lag so that one fermentor is connected to the primary distillation step when the other fermentor is disconnected. A fermentor disconnected after a finished fermentation cycle contains an amount of fermentation liquor, which corresponds to the stream of intermediate stillage (i.e. the bottom stream from the primary distillation step) to the secondary distillation step during a time in the order of 25 hours. The disconnected fermentor is suitably emptied by feeding its fermentation liquor to the secondary distillation step during an extended time, for example 80 hours, which increases the supply stream to the same, in this case with about 30%.

Since the ethanol productivity of the yeast decreases during a part of the period during which the fermentor is connected to the primary distillation step and a constant ethanol supply to the distillation plant is desired, the fermentor is suitably dimensioned so that the desired ethanol production can be achieved also in the end of the operation period when the ethanol productivity of the yeast is the lowest. This means that the maximum production capacity is not utilized during the first part of the operation period, during which the ethanol production is limited by the supply of fermentable sugar to the fermentor. One advantage of underdimensioning the feed of fermentable substance with respect to the maximum fermentation capacity is a somewhat further reduction of the constant low concentration of fermentable substance in the fermentor and the corresponding yield improvement due to reduced losses of fermentable material in the stillage. However, if utilization of the maximum ethanol productivity of the yeast and the fermentor is desired, the process according to the present invention can of course be carried out so that a decreasing ethanol production is obtained during the operation period of the fermentor. Nevertheless, a very interesting aspect of the present invention resides in the possibility of achieving constant ethanol flow through the primary distillation step during unlimited time and without buffer tanks by means of only two alternating fermentors while, compared with corresponding recirculation process with only one fermentor connected during longer time, a much more concentrated stillage is obtained from the secondary distillation step, the energy supply thereto being the same.

The invention will now be further illustrated with reference to the accompanied drawing, which shows a flow sheet of a preferred embodiment of the invention. In the drawing, unbroken flow lines refer to a continuous circuit with a fermentor FI connected to a primary distillation step PD. From a substrate preparation step (not shown) a molasses substrate is fed through line 1, valve 2 and line 3 to fermentor FI. From the top of the fermentor carbon dioxide is discharged through 4, and from the bottom of the fermentor fermentation liquor is withdrawn through line 5, valve 6 and line 7 to a centrifugal separation step C in which the fermentation liquor is separated in a yeast-enriched stream 8, which is recirculated to fermentor FI through valve 9 and line 10, and one essentially yeast-free stream 11, which is supplied to the primary distillation column PD. From the top of the distillation column PD an ethanol enriched vapour stream is discharged through 12 and from the bottom of the column a liquid stream is discharged through 13, one part 14 of which is recirculated through valve 15 and line 16 to fermentor FI and the residual part 17 is sent to the secondary distillation step SD. The residual ethanol of the stream 17 is stripped off in the secondary distillation step by means of indirect heating 18 and the vapour stream 19 thereby produced is introduced in the primary distillation step as direct steam. From the bottom of the secondary distillation step a concentrated stillage 20 is discharged.

The dotted flow lines illustrate the connection to the primary distillation step PD of a further, with fermentor FI alternating fermentor FII just by switching valves so that fermentor FI simultaneously is disconnected from the circuit. Therefore, the same reference figures have been used for the lines corresponding to the above stated lines for fermentor FI with the addition of the letter a. Further dotted flow lines are also drawn to show how a fermentor taken out of operation can be emptied by charging its fermentation liquor to the secondary distillation step SD. The fermentor FII is connected to the continuous circuit by switching valves 6, 6a, 9, 2 and 15, while fermentor FI is disconnected thereby to be emptied from its fermentation liquor through lines 21 and 22 to the secondary distillation step SD.

EXAMPLE 1

The example refers to continuous fermentation during a longer period of time (250 hours) in a fermentor under steady-state condition.

A fermentor with a total liquid volume of 10 m$^3$ was charged with 0.7 m$^3$ prepropagated yeast culture of yeast species Schizosaccharomyces Pombe and further filled during 20 hours with a diluted substrate of cane sugar molasses containing 11.6% by weight fermentable sugar. To promote yeast growth also smaller amounts of ammonia and phosphoric acid were added to the fermentor and air was continuously blown through the liquid in the fermentor. The fermentation temperature was thermostatically controlled to 32° C., and pH in the fermentor was controlled to 4,8. The fermentor was filled to a liquid volume of 7 m$^3$.

The filled fermentor was connected to the primary distillation step PD in a distillation plant, described above. 650 kg/h cane sugar molasses with a concentration of fermentable sugar (F) of 19.4% by weight and a concentration of non-fermentable material (NF) of 15.5% by weight. The recirculation ratio was controlled so that steady-state was maintained in the system. The recirculation ratio was 0.57, i.e. 57% of the bottom stream discharged from the primary distillation step PD was recirculated to the fermentor. After continuous fermentation during 250 hours the following stream compositions were determined:

TABLE 1

| Comp | 3 Feed substrate | | 11 Mash to PD | | 12 Vapour from PD | | 13 Intermediate stillage from PD | | 20 Stillage from SD | |
|---|---|---|---|---|---|---|---|---|---|---|
| | kg/h | % b.w. | kg/h | % b.w. | kg/h | % b.w. | kg/h | % b.w. | kg/h | % b.w. |
| F | 126 | 19,4 | 3 | 0,2 | | | 3 | 0,2 | 1 | 0,3 |
| NF | 101 | 15,5 | 233 | 16,8 | | | 233 | 16,7 | 101 | 22,5 |
| Water | 423 | | 1070 | | 82 | | 1144 | | 340 | |
| Ethanol | | | 62 | 4,5 | 58 | 40,8 | 7 | 0,5 | | |
| Total | 650 | | 1380 | | 142 | | 1398 | | 447 | |

From the values of table 1 it can be concluded that at long time steady-state fermentation in a fermentor fed with a cane sugar molasses substrate containing 19.4% fermentable sugar and 15.5% NF it is possible to maintain a DS-concentration in the fermentor of about 16% by weight and a DS-concentration in the discharged stillage of 22.8% by weight. The ethanol productivity was after 250 hours 8.3 kg/m$^3$/h.

EXAMPLE 2

The fermentor was filled during 20 hours with the same molasses substrate and the same yeast culture as used in example 1, however this time up to a liquid volume of about 10 m$^3$. The DS-content of non-fermentable material in the fermentor was 9.6% by weight.

The fermentor was then connected to the same distillation equipment as used in example 1. 460 kg/h of the same cane sugar molasses as used in example 1, however now having a concentration of 30.2% by weight fermentable sugar and a NF-content of 24.1% by weight, was continuously fed to the fermentor. The water content of the substrate was thus reduced to 46% by weight compared with 65% by weight in the steady-state run according to example 1. The ratio recirculated intermediate stillage from the primary distillation step was raised to 73%. Continuous supply of fermentation liquor from the fermentor to the primary distillation step, continuous recirculation of a part of the intermediate stillage from the primary distillation step and final stripping of the residual part of the intermediate stillage were maintained during 120 hours. The content of non-fermentable substance (NF) in the fermentor and the content NF in the discharged stillage increased during this time to end values 27.5% by weight and 50.6% by weight respectively. The NF-concentration at different moments of the fermentation are stated in table 2 below. Samples were also taken during the fermentation to determine the number of bacteria in the fermentor liquid. The result is shown in table 2.

TABLE 2

| Operation time hours | NF in fermentor % by weight | NF in stillage % by weight | Number of bacteria/ml in fermentor × 10$^6$ |
|---|---|---|---|
| 0 | 9,6 | 11,0 | 12 |
| 20 | 17,8 | 26,5 | 18 |
| 40 | 23,2 | 39,2 | 20 |
| 80 | 26,1 | 46,8 | 1,3 |
| 120 | 27,5 | 50,6 | 1,4 |

From the samples collected during the fermentation run also the average values for the NF-content in the fermentor and in the discharged stillage were calculated, being 22.3% by weight and 39.3% by weight, respectively. During the continuous process, the average production of ethanol was 63 kg/h, from which the ethanol productivity in the fermentor filled to 10 m$^3$ is calculated to about 6.3 kg/m$^3$/h. The bacteria values stated in table 2 indicate a clear reduction of the amount of living bacteria when a concentration of non-fermentable material in the fermentor is in the order of 20% by weight DS or higher.

I claim:

1. A process for the production of ethanol through fermentation of beet or cane sugar molasses by means of yeast in a fermentor (FI), in which a stream (5) of fermentation liquor with an ethanol content of 3–7% by weight and a content of fermentable material less than 2% by weight is continuously withdrawn from the fermentor, said stream (5) is separated in a centrifugal separation step (C) into a yeast enriched stream (8), which is recirculated to the fermentor (FI), and into an essentially yeast free stream (11), which in a primary distillation step, (PD) is separated into an ethanol enriched top stream (12) and a residual liquid bottoms stream (13), a part of which is recirculated to the fermentor (FI) and the remaining part (17) is supplied to a secondary distillation step (SD) for stripping off remaining ethanol and forming a concentrated ethanol free stillage (20), which is discharged, characterized in that the input of process water is controlled so that during a first period of time the concentration of nonfermentable substance in the fermentor (FI), calculated as water free substance (DS), increases from a starting value in the range of 5 to 15% by weight DS to a value in the range of 20 to 30% by weight DS, in which latter range the ethanol productivity of the yeast decreases, and in that fermentation and distillation with recirculation of said bottoms stream (14) is continued at said last concentration of nonfermentable substance in the fermentor during the second period of time, the average concentration of nonfermentable substance in the fermentor over said two periods of time exceeding 20% by weight DS.

2. A process according to claim 1, characterized in that the average concentration of non-fermentable substance in the fermentor (FI) is maintained above 22% by weight DS.

3. A process according to claim 1 or 2, characterized in that said part (17) of the bottom stream (13) from the primary distillation step (PD) is separated in the secondary distillation step (SD) into an ethanol containing vapour stream (19) and an ethanol-free stillage stream (20) having an average DS-content exceeding 35% by weight, and that said ethanol containing vapour stream (19) is supplied to the primary distillation step (PD) in the form of a direct steam, which constitutes the essential part of the heat energy required for operating the primary distillation step.

4. A process according to claim 3, characterized in that the average DS-content in the stillage stream (20) from the secondary distillation step (SD) exceeds 38% by weight.

5. A process according to claim 1, characterized in that said fermentor (FI) is one of at least two fermentors (FI, FII) which are alternately connected to said primary distillation step (PD).

6. A process according to claim 3, characterized in that the secondary distillation step (SD) is also supplied with fermentation liquor (22) from a fermentor (FII), which, after a finished operation period in circuit with the primary distillation step (PD), is disconnected from the same.

7. A process according to claim 1, characterized in that the yeast species used for the fermentation is Schizosaccharomyces Pombe.

8. The process claimed in claim 1 wherein the input of process water is controlled by controlling the concentration of fermentable material in the steam of fermentation liquor.

* * * * *